(12) United States Patent
Khan et al.

(10) Patent No.: US 8,158,162 B2
(45) Date of Patent: Apr. 17, 2012

(54) EUTECTIC-BASED SELF-NANOEMULSIFIED DRUG DELIVERY SYSTEM

(75) Inventors: Mansoor A. Khan, Vienna, VA (US); Sami Nazzal, Monroe, LA (US)

(73) Assignee: Jarrow Formulas, Inc., Los Angeles, CA (US)

( * ) Notice: Subject to any disclaimer, the term of this patent is extended or adjusted under 35 U.S.C. 154(b) by 0 days.

(21) Appl. No.: 12/493,406

(22) Filed: Jun. 29, 2009

(65) Prior Publication Data

US 2010/0166873 A1 Jul. 1, 2010

Related U.S. Application Data

(62) Division of application No. 10/293,932, filed on Nov. 14, 2002, now Pat. No. 7,588,786.

(60) Provisional application No. 60/331,292, filed on Nov. 14, 2001.

(51) Int. Cl.
*A61K 36/00* (2006.01)
*A61K 36/752* (2006.01)
(52) U.S. Cl. ........................ 424/725; 424/736
(58) Field of Classification Search ............... None
See application file for complete search history.

(56) References Cited

U.S. PATENT DOCUMENTS

| | | | |
|---|---|---|---|
| 4,029,760 A | 6/1977 | De Roeck born Holtzhauer | |
| 4,559,222 A | 12/1985 | Enscore | |
| 5,229,268 A * | 7/1993 | Pry et al. | 435/7.92 |
| 5,290,605 A | 3/1994 | Shapira | |
| 5,298,246 A | 3/1994 | Yano et al. | |
| 5,431,916 A | 7/1995 | White | |
| 5,503,862 A * | 4/1996 | Fuisz et al. | 426/548 |
| 5,858,401 A | 1/1999 | Bhalani | |
| 5,968,987 A | 10/1999 | Charman | |
| 5,980,939 A | 11/1999 | Kim | |
| 6,096,338 A | 8/2000 | Lacy | |
| 6,121,234 A | 9/2000 | Benet | |
| 6,174,547 B1 | 1/2001 | Dong | |
| 6,197,349 B1 | 3/2001 | Westesen et al. | |
| 6,200,550 B1 | 3/2001 | Masterson et al. | |
| 6,207,137 B1 | 3/2001 | Shuch | |
| 6,284,268 B1 | 9/2001 | Mishra | |
| 6,368,618 B1 * | 4/2002 | Jun et al. | 424/449 |
| 6,503,483 B2 | 1/2003 | Shuch | |
| 6,552,004 B1 | 4/2003 | Elazhary | |
| 6,630,170 B2 | 10/2003 | Balkus | |
| 6,730,319 B2 | 5/2004 | Maeder et al. | |
| 6,790,465 B2 | 9/2004 | Weissman | |
| 2002/0102280 A1 | 8/2002 | Anderson | |
| 2003/0108600 A1 | 6/2003 | Okibayashi et al. | |
| 2003/0147927 A1 | 8/2003 | Khan | |
| 2004/0047922 A1 | 3/2004 | Elstner | |

FOREIGN PATENT DOCUMENTS

| | | |
|---|---|---|
| JP | S57-42616 | 3/1982 |
| JP | S57-142911 | 9/1982 |
| WO | WO 98/56368 | 12/1998 |

OTHER PUBLICATIONS

DW 1997-225833, Apr. 1997, WO 9711688 or D, Bon C.*
U.S. Appl. No. 60/253,874, filed Nov. 29, 2000, Anderson.
T. Kommuru, et al., "Stability of Bioequivalence Studies of Two Marketed Formulations of Coenzyme Q10 in Beagle Dogs", Jul. 1999.
T. Kommuru, et al., "Self-emulsifying drug delivery systems (SEDDS) of coenzyme Q10: formulation development and bioavailability assessment", Jan. 2001.
Y. Kaplun-Frischoff, et al., "Testosterone Skin Permeation Enhancement by Menthol Through Formation of Eutectic with Drug and Interaction with Skin Lipids", Dec. 1997.
A. Shojaei, et al., "Transbuccal Permeation of a Nucleoside Analog, Dideoxycytidine: Effects of Menthol as a Permeation Enhancer", Dec. 1999.
L. Kang, et al., "Physicochemcial Studies of Lidocaine-Menthol Binary Systems for Enhanced Membrane Transport", Sep. 2000.
C. Pouton, et al., "Lipid Formulations for Oral Administration of Drugs: Non-emulsifying, Self-emulsifying and 'Self-microemulsifying' Drug Delivery Systems", Oct. 2000.
Nutramax CoMax Q10 Trademark Registration and Specimen, filed Jul. 31, 1992.
Nutramax CoMal Q10 Trademark Registration and Specimen, filed Oct. 26, 1993.
Prosecution history of USPN 7,588,786 to Khan, Sep. 15, 2009.

* cited by examiner

*Primary Examiner* — Christopher R Tate
*Assistant Examiner* — Randall Winston
(74) *Attorney, Agent, or Firm* — McCarter & English, LLP

(57) ABSTRACT

A eutectic-based self-nanoemulsified drug delivery system (SNEDDS) is formulated from polyoxyl 35 castor oil (Cremophor), medium chain mono- and diglycerides (capmul), essential oils, and a pharmacologically effective drug. The preferred pharmacologically effective drug is a poorly water soluble drug, such as ubiquinone ($CoQ_{10}$). The SNEDDS can be further incorporated into a powder to produce a solid dosage form. The solid dosage form contains the SNEDDS, a copolymer of vinylpyrrolidone and vinyl acetate (Kollidon VA 64), maltodextrin, and microcrystalline cellulose (MCC).

19 Claims, 12 Drawing Sheets

EUTECTIC-BASED SELF-NANOEMULSIFIED DRUG DELIVERY SYSTEM

CROSS-REFERENCE TO RELATED APPLICATIONS

This application is a Divisional of U.S. patent application Ser. No. 10/293,932; filed: Nov. 14, 2002, now U.S. Pat. No. 7,588,789 which claims the benefit, under 35 U.S.C. 119(e), of U.S. Provisional Application No. 60/331,292 filed Nov. 14, 2001, the contents of which are incorporated herein by reference.

BACKGROUND OF THE INVENTION

1. Field of the Invention

The present invention relates generally to a eutectic-based self-nanoemulsified drug delivery system (herein referred to as "SNEDDS"). The eutectic-based SNEDDS is preferably used to administer poorly water soluble drugs to a patient.

2. Description of Related Art

Large proportions of new drug candidates have poor water solubility. To overcome these problems, various formulation strategies were reported, including complexation with cyclodextrin, solid dispersions and co-precipitates. In recent years, however, much attention has been focused on lipid based formulations, with particular emphasis on self-emulsifying drug delivery systems (herein referred to as "SEDDS"). SEDDS are isotropic mixtures of oil, surfactant, co-surfactant and drug that form fine oil-in-water emulsion when introduced into aqueous medium under gentle agitation.

Ubiquinone, also known as Coenzyme $Q_{10}$ (herein referred to as "$CoQ_{10}$"), is an important component of the mitochondrial respiratory chain. The structure of $CoQ_{10}$ is as follows:

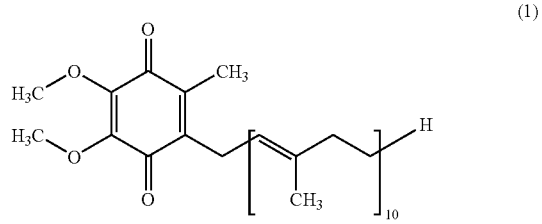

(1)

Because of its poor water solubility, $CoQ_{10}$ presents a challenge when developing a formulation for oral administration. Many approaches have been used to improve the in vitro dissolution of $CoQ_{10}$. Some of the approaches include complexation with cyclodextrins, solubilization in a blend of polysorbate 80 and medium chain triglycerides, preparation of redispersible dry emulsion, solid dispersion, and recently, development of a self-emulsified drug delivery system (SEDDS).

In the traditional methods of preparing self-emulsified delivery systems, active ingredients are dissolved in fixed oils or triglycerides and subsequently blended with suitable solubilizing agents. However, due to limited solubility of some drugs, such as $CoQ_{10}$, in these oils, such methods often result in low drug loading and suffer from irreversible precipitation of the active ingredient and/or the excipient with time.

Emulsion systems based on a eutectic mixture of lidocaine-prilocaine and lidocaine-menthol were used in preparation of topic formulations. However, little is known about the use of eutectic mixtures for the preparation of self-emulsified formulation.

Formulations containing SEDDS also require filling into soft or hard gelatin capsules. Therefore, the incorporation of self-emulsifying vehicles into a powder to produce solid dosage forms would be of great interest. Recently, pellets containing a self-emulsifying mixture were prepared by extrusion-spheronization. Solid-state microemulsion for the delivery of cyclosporin also was prepared by coating the premicroemulsion with an enteric material. Similarly, a solvent-evaporation method was used to prepare tocopheryl nicotinate tablets using calcium silicates as the adsorbing agent. Such methods often require elaborate processing and instrumentation.

On the other hand, solid solutions and liquisolids were produced by blending liquid medications with selected powder excipients to produce free-flowing, readily compressible powders. Such excipients include cellulose or lactose as the carriers and fine silicates as the coating material. Using a similar approach, a solid dosage form based on microemulsion adsorbed onto colloidal silicon dioxide and microcrystalline cellulose was introduced. In most cases as well as in the case of liquisolids, however, adsorbed oil- or lipid-based formulations form a thin film of oil on the surface of the powder. This film causes particles to adhere and produces a mass that exhibits poor flow and tableting characteristics. To improve flow and compaction properties, oil loading is reduced, or fine particulates such as silicates are added in quantities often exceeding the limits stated by the Code of Federal Regulations.

BRIEF SUMMARY OF THE INVENTION

To overcome the foregoing problems, a eutectic-based semisolid self-nanoemulsified drug delivery system (SNEDDS) was formed as an alternative to the conventional self-emulsifying vehicles. The SNEDDS contains polyoxyl 35 castor oil (herein referred to as "Cremophor") as a surfactant, a medium chain mono- and diglyceride (herein referred to as "Capmul") as a co-surfactant, essential oils, and a pharmacologically effective drug. The preferred amount of Cremophor is 23-31 wt %. The preferred amount of Capmul is 23-31 wt. %. The preferred amount of essential oils is 19-26 wt. %. The preferred amount of the pharmacologically effective drug is 19-26 wt. %. The essential oils are preferably volatile oils selected from the group comprising menthol, spearmint oil, peppermint oil, lemon oil, anise oil and mixtures thereof. Preferably, the pharmacologically effective drug is a drug having poor water solubility. The preferred pharmacologically effective drug is ubiquinone (herein referred to as "$CoQ_{10}$"). The SNEDDS is in the form of a semi-solid mass that is then introduced into soft or hard gelatin capsules.

A SNEDDS contains an isotropic mixture of oil, surfactant, co-surfactant and drug, which forms a fine oil-in-water emulsion when introduced into an aqueous medium under gentle agitation. In a eutectic-based SNEDDS, the melting point depression method allows the oil phase containing the drug itself to melt at body temperature from its semisolid consistency and disperse to form emulsion droplets in nanometer size range. The SNEDDS improves the dissolution of poorly soluble compounds, such as the preferred $CoQ_{10}$.

The SNEDDS may be further incorporated into a powder to produce a solid dosage form. The solid dosage form contains the SNEDDS and the following powdered ingredients: a copolymer of vinylpyrrolidone and vinyl acetate (herein referred to as "Kollidon VA 64"), maltodextrin and microcrystalline cellulose (herein referred to as "MCC"). The powder ingredients are added to the SNEDDS to provide a solid dosage form having preferably 3-35 wt. % Kollidon VA 64, 35-82 wt. %. maltodextrin, 11-47 wt. % MCC and an effective amount of a SNEDDS for administering said pharmacologically effective drug to a patient.

In a preferred embodiment, when eutectic-based SNEDDS of $CoQ_{10}$ are mixed with small quantities of the Kollidon VA 64 a wax-like copolyvidone paste is formed. Kollidon VA 64 possesses a unique dry-binding capacity. Copolyvidone paste ground with a suitable excipient produces granules with good flow properties that are readily available for direct compression. Maltodextrin was found to be a good grinding agent due to its solubility, particle size, and acceptable adsorbing properties. When compressed, however, the given mixture of the copolyvidone paste and maltodextrin produced soft compacts. Therefore, directly compressible microcrystalline cellulose was added. MCC often is regarded as one of the best excipients for direct compression. Extragranular MCC was shown to increase dissolution rates and compressibility of tablets made by high-shear granulation.

BRIEF DESCRIPTION OF THE SEVERAL VIEWS OF THE DRAWINGS

The features and advantages of the present invention will become apparent from the following detailed description of a preferred embodiment thereof, taken in conjunction with the accompanying drawings, in which.

DETAILED DESCRIPTION OF THE INVENTION

Figure 1:
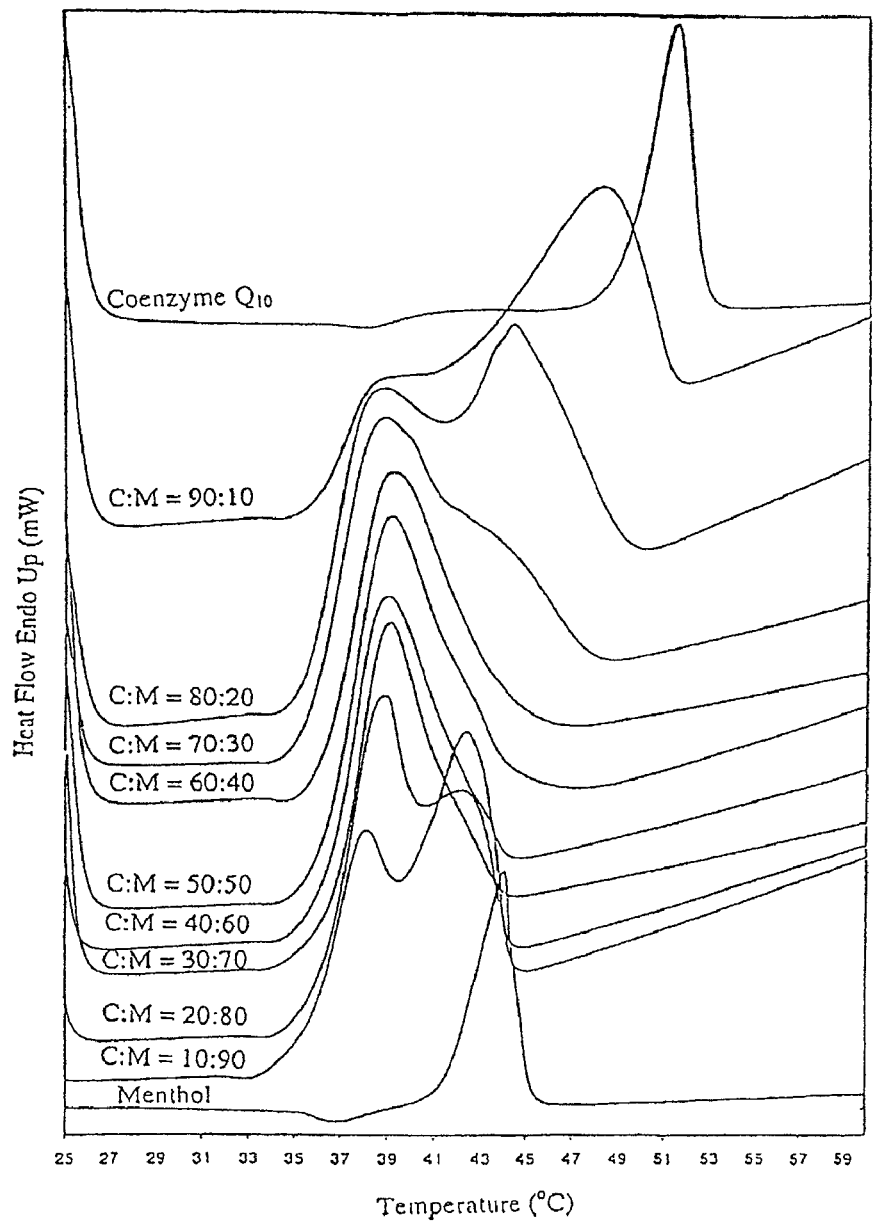
FIG. 1 shows DSC thermograms of $CoQ_{10}$, L-menthol, and their binary mixtures (ratios by weight)

The present invention is directed to a eutectic-based self-nanoemulsified drug delivery system (herein referred to as "SNEDDS") containing an isotropic mixture of oil, surfactant, co-surfactant and a pharmacologically effective drug. The oil present in the SNEDDS is an essential oil that is a volatile oil, preferably selected from the group comprising menthol, spearmint oil, peppermint oil, lemon oil, anise oil and mixtures thereof. The essential oils in the SNEDDS are present in a preferred amount of 19-26 wt. %. The pharmacologically effective drug present in the SNEDDS is preferably a poorly water soluble compound, preferably selected from the group comprising drugs or dietary supplements, or nutraceuticals with a log P value over 3. Most preferably, the pharmacologically effective drug is ubiquinone (herein referred to as "$CoQ_{10}$"). Other preferred pharmacologically effective drugs include, but are not limited to, cyclosporines and Vitamin E. The preferred amount of the pharmacologically effective drug in the SNEDDS is 19-26 wt. %. The surfactant in the SNEDDS is preferably polyoxyl 35 castor oil (herein referred to as "Cremophor") in a preferred amount of 23-31 wt. %. The co-surfactant in the SNEDDS is preferably a medium chain mono- and diglyceride (hereafter, "Capmul") in a preferred amount of 23-31 wt. %. The preferred ratio of Cremophor to Capmul is 0.5-1.5. A preferred SNEDDS containing 23 wt. % lemon oil, 23 wt. % $CoQ_{10}$, 27 wt % Cremophor, and 27 wt. % Capmul releases 93.4% CoQ.sub.10. The SNEDDS produces a semi-solid mass which is filled into soft or hard gelatin capsules. In a preferred embodiment, the SNEDDS are filled into hydroxypropyl methylcellulose (HPMC) capsules.

The SNEDDS may be further incorporated into a powder to produce a solid dosage form by combining the SNEDDS with the following powder ingredients: a copolymer of vinylpyrrolidone and vinyl acetate (herein referred to as "Kollidon VA 64"), maltodextrin and microcrystalline cellulose (herein referred to as "MCC"). The preferred MCC is Avicel MCC, which is available in many grades that differ from each other by their particle size, particle shape, and moisture content, obtained from FMC Corp. (Newark, Del.). Table 1 shows the physicochemical properties of the preferred Avicel MCC. Avicel PH 105 produces a sustained release tablet dosage form.

TABLE 1

| Avicel MCC Grade | Average Particle Size (•m) | Moisture Content (%) |
|---|---|---|
| Avicel PH-105 | 20 | •5 |
| Avicel PH-101 | 50 | •5 |
| Avicel PH-113 | 50 | •2 |
| Avicel PH-102 | 90 | •5 |
| Avicel PH-112 | 90 | •1.5 |
| Avicel PH-200 | 180 | •5 |

Various MCC grades with different particle size and moisture contents vary in their adsorbing capacity, as shown below in the preferred embodiment illustrated in Example II. Although an MCC with a smaller particle size such as Avicel PH-105 provides a greater surface area for oil adsorption, it shows a reduction in compatibility and tensile strength. On the other hand, Avicel PH-112, which has larger particles and reduced adsorbing capacity, demonstrated improved hardness and compaction. The initial size of the particles constituting a powder is an important factor in determining its compaction behavior. For most powdered materials, compaction of the small particles results in stronger tablets because of the large surface area available for bonding. The powder ingredients are added to the SNEDDS to provide a solid dosage form having preferably 3-35 wt. % Kollidon VA 64, 35-82 wt. %. maltodextrin, 11-47 wt. % MCC, and an effective amount of a SNEDDS for administering said pharmacologically effective drug to a patient. In a preferred embodiment, the optimum amount of SNEDDS added to a solid dosage form is determined by maximizing the amount of the pharmacologically effective drug emulsified into a dissolution medium within 45 minutes. In a preferred embodiment wherein $CoQ_{10}$ is the pharmacologically effective drug, 46.1-91.1 wt. % $CoQ_{10}$ was released from the solid dosage form within 45 minutes. A preferred solid dosage form containing 7.8 wt. % Kollidon VA 64, 65.4 wt. % maltodextrin, 11.7 wt. % MCC, and 15.1 wt. % SNEDDS release 85.4% of $CoQ_{10}$. The SNEDDS is this preferred solid dosage form contained an oily mix of $CoQ_{10}$ and lemon oil in a ratio of 1:1. Cremophor EL and Capmul MCM-C8 were added to the oily mix at a final concentration of 26.9% w/w each.

EXAMPLE I

The present example illustrated the use of eutectic mixtures with essential oils for the preparation of SNEDDS. Prepared SNEDDS improve the dissolution of poorly water soluble drugs, such as $CoQ_{10}$. Recrystallization adds to the stability of the drug while providing attractive semisolid preparation that could be filled into hard capsules. Turbidimetry directly correlates emulsification rate, lag times and droplet size with formulation ingredients. This was used to distinguish between different self-emulsified preparations, which might be more important than simply identifying systems that are spontaneously emulsifying.

Differential Scanning Calorimetry (DSC) of $CoQ_{10}$-menthol and $CoQ_{10}$-essential Oil Binary System $CoQ_{10}$ and L-menthol were mixed at various ratios between 90:10 and 10:90 (w/w). Approximately 5 mg of the mixture was sealed in an aluminum pan and analyzed using a differential scanning calorimeter (DSC 7, Perkin-Elmer, Norwalk, Conn.). Thermal analysis was carried out between 25 and 60° C. under nitrogen gas flow against an empty reference pan at a heating rate of 10° C. $min^{-1}$. Similarly, different ratios of $CoQ_{10}$ and the essential oil between 80:20 and 20:80 (w/w) were mixed and melted at 37° C. Resulting oils were stored at 4° C. for 24 hours to allow complete re-crystallization of $CoQ_{10}$. To avoid oil evaporation, approximately 10 mg of the mixture was weight onto a DSC sample pan and kept in an airtight container during storage prior to DSC analysis. For $CoQ_{10}$-essential oil mixtures at ratios between 80:20 and 60-40 (w/w), thermal analysis was carried out between 25 and 55° C. Heating rate used was 10° C. $min^{-1}$. Lower temperatures were maintained using refrigerated cooling accessory (Intracooler 2, Perkin-Elmer).

Figure 2:
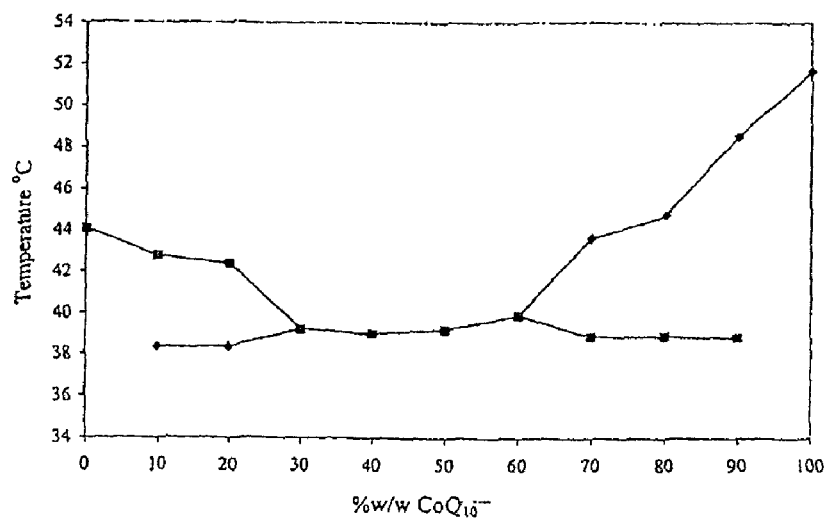
FIG. 2 is a temperature/composition phase diagram of $CoQ_{10}$-menthol binary system determined by DSC.
Figure 3:
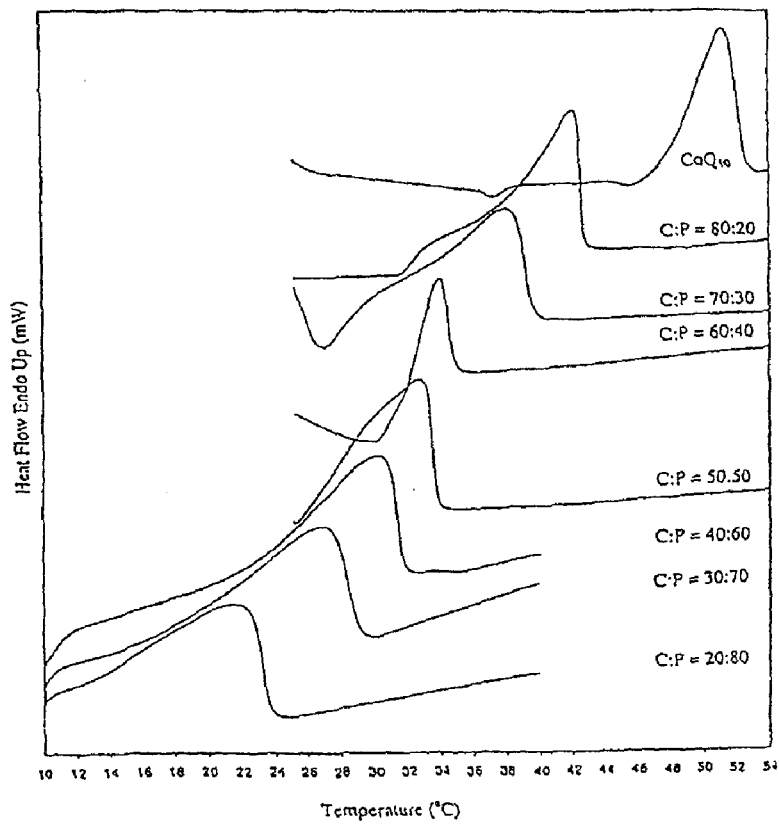
FIG. 3 shows DSC thermograms of $CoQ_{10}$, peppermint oil, and their binary mixtures (ratios by weight)
Figure 4:
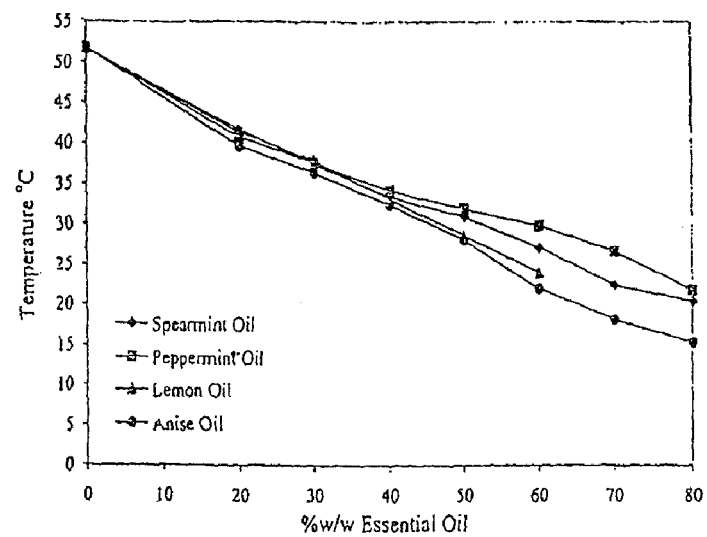
FIG. 4 is a temperature/composition phase diagram of $CoQ_{10}$-essential oil binary systems determined by DSC.

$CoQ_{10}$ was found to form a eutectic mixture with L-menthol. DSC thermograms of the binary system of $CoQ_{10}$ with menthol at different ratios are given in FIG. 1. The major endotherms at 51.7 and 44.1° C. represent the melting point of $CoQ_{10}$ and L-menthol, respectively. Based on the thermal analysis data a binary phase diagram was constructed and is given in FIG. 2. As seen from FIG. 2, the eutectic melting point lies between 30 and 60% w/w $CoQ_{10}$. Within the binary system, depression in melting temperature of $CoQ_{10}$, however, was limited to temperatures exceeding 37° C. Thus, an oily melt can not be obtained at or below body temperature. A gradual shift and reformation of the original $CoQ_{10}$ endothermic peak was observed when the samples within the binary system were left uncovered and analyzed after 1 week. The volatile ingredients of menthol are responsible for the physical changes in $CoQ_{10}$, i.e. depression in its melting temperature. To validate this observation, the effect of peppermint oil as a representative volatile ingredient of menthol crystals and three additional volatile oils namely, spearmint oil, lemon oil and anise oil were investigated for their effect on the melting thermograms of $CoQ_{10}$. Thermal analysis and the DSC data of the binary system of $CoQ_{10}$ with peppermint oil are given in FIG. 3. A binary phase diagram of $CoQ_{10}$ with the essential oils was constructed and is given in FIG. 4. Thermograms of the mixtures clearly indicated that these compounds formed binary eutectic systems. An increase in percent essential oil causes a gradual decrease in the melting temperature of $CoQ_{10}$. At sufficient concentration of the volatile oil it becomes feasible to convert $CoQ_{10}$ into an oily phase at or below body temperatures.

Determination of CoQ10 Melting Time $CoQ_{10}$ was accurately weighed and mixed with 50 and 60% w/w of peppermint oil, spearmint oil, anise oil or lemon oil in a screw-capped glass vials. Mixtures were allowed to melt at 37° C. in water bath (Ikamag® Ret-G, Terochem Scientific, Toronto, Canada). Cremophor EL was added to the melt at a concentration of 20, 40 and 60% w/w of the final weight using a positive displacement pipette (Microman®, Gilson Inc., Middleton, Wis.) and stirred with a magnetic bar. Vials were then capped and stored at ambient temperatures in tight containers protected from light. After 24 hours sample vials containing the solidified preparation were immersed in water bath maintained at 37° C. Samples were monitored for a change in their physical appearance and the time was recorded until a complete melt was obtained.

Due to the limited solubility of $CoQ_{10}$ in fixed oils and triglycerides, the melting point depression method using essential oils provides an attractive alternative for the preparation of an emulsified formulation. A number of essential oils are used for their flavors and odors and are recognized by the Code of Federal Regulations as GRAS (generally recognized as safe) compositions that do not require regulatory agency approval before they are included in ingested material. A preparation could be made at which body temperature is used to melt a system comprising essential oil, $CoQ_{10}$ and an emulsifier when the essential oil is added in an amount sufficient to lower the melting temperature of $CoQ_{10}$ to or below 37° C. Essential oils, however, should be effective as eutectic agents in the presence of other liquid excipients. Table 2 demonstrates the feasibility of the described approach by showing the melting time, in minutes, for the given mixture of $CoQ_{10}$, essential oil and cremophor EL at 37° C. Four essential oils, spearmint oil, peppermint oil, lemon oil, and anise oil, were evaluated for their eutectic efficacy in the presence of other formulation excipients. The essential oil percentage rates in Table 2 are the percent w/w of essential oil in the binary mixture of the essential oil with $CoQ_{10}$. The Cremophor EL (CrEL) percentage rates in Table 2 are the percent w/w of Cremophor EL in the final mixture of $CoQ_{10}$, essential oil and cremophor EL. The N/A indication in Table 1 indicates the formulations where no melting time was observed within 24 hours.

TABLE 2

| CrEL (%) | 20% | 40% | 60% |
|---|---|---|---|
| Spearmint Oil | | | |
| 60% | 0.69 ± 0.13 | 1.56 ± 0.59 | N/A |
| 50% | 4.38 ± 2.13 | N/A | N/A |
| Peppermint Oil | | | |
| 60% | 1.11 ± 0.42 | N/A | N/A |
| 50% | 8.17 ± 2.08 | N/A | N/A |
| Anise Oil | | | |
| 60% | 0.83 ± 0.73 | 0.97 ± 0.27 | N/A |
| 50% | 1.28 ± 0.63 | 2.33 ± 0.88 | N/A |
| Lemon Oil | | | |
| 60% | 1 ± 0.17 | 1.29 ± 0.44 | 1.76 ± 0.23 |
| 50% | 2 ± 0.29 | 3.56 ± 1.69 | 5.33 ± 1.48 |

Due to limited solubility of $CoQ_{10}$ in surfactant, the use of cremophor EL as a model emulsifier not only induces crystallization of $CoQ_{10}$ in the cooled supersaturated mixture but also may delay or retard re-melting the system at higher temperatures. The time necessary to melt different combinations of $CoQ_{10}$, essential oil and cremophor EL at 37° C. was recorded. When 60% w/w of cremophor EL was added, preparations made with 50 and 60% w/w lemon oil to $CoQ_{10}$ melted within 5.3 and 1.8 min, respectively. Precipitation of $CoQ_{10}$ at higher cremophor EL concentration for the formulas made with anise oil, peppermint oil and spearmint oils was however irreversible rendering them less effective for the preparation of emulsified systems. The use of lemon oil appears reasonable and attractive. At 50% w/w of lemon oil to $CoQ_{10}$, formulas would melt within 5 min from initial exposure to body temperatures. In this case, recrystallization of $CoQ_{10}$ becomes advantageous in the production of a stable semisolid product compared with the existing liquid formulas with the potential of irreversible precipitation and separation of the active ingredient due to supersaturation or fluctuation in storage temperatures. Furthermore, lemon oil has been used internally as herbal medicine for acidic disorders such as arthritis and rheumatism with great benefit in liver congestion.

Visual Observations

To assess the self-emulsification properties, formulation (50 mg) pre-melted at 37° C. was introduced into 100 ml of water in a glass Erlenmeyer flask at 25° C. and the contents were gently stirred manually. The tendency to spontaneously form a transparent emulsion was judged as 'good', and it was judged 'bad' when there was poor or no emulsion formation. Phase diagrams were constructed identifying the good self-emulsifying region. All studies were repeated in triplicates with similar observation being made between repeats.

Figure 5:
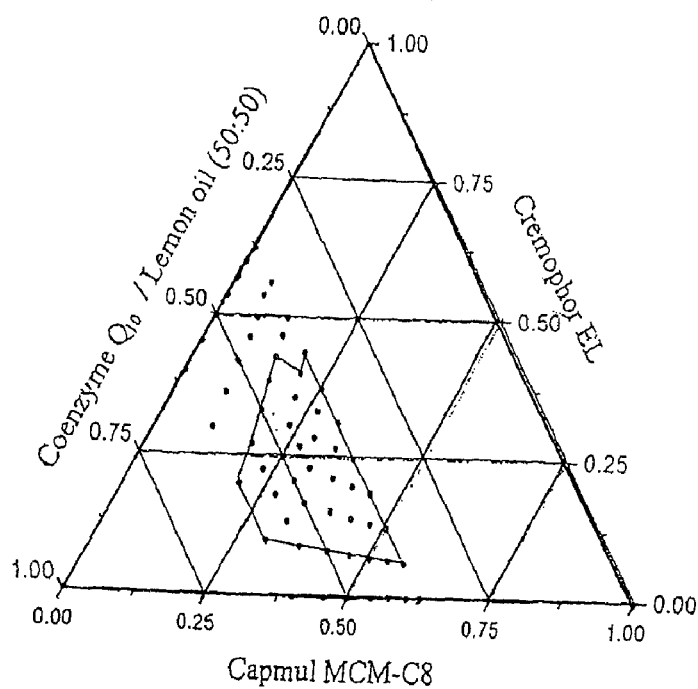
FIG. 5 is a pseudo-ternary phase diagram indicating the efficient self-emulsification region.

For the development of a self-emulsified formulation, a right blend of low and high HLB surfactants is necessary for the formation of a stable microemulsion. Therefore, a high HLB surfactant, cremphor EL, and a low HLB co-surfactant, capmul MCM-C8, were selected. A ratio of 50:50 of lemon oil to $CoQ_{10}$ was selected as the oil phase. The pseudo ternary phase diagram of the system comprising the surfactant, co-surfactant and the oily phase was constructed and is give in FIG. 5. The area enclosed within the solid line represents the region of self-emulsification. Within this area a ternary mixture forms a fine oil in water emulsion with only gentle agitation. This is possible as surfactant strongly localized to the surface of the emulsion droplet reduces interfacial free energy and provide a mechanical barrier to coalescence resulting in a thermodynamically spontaneous dispersion. Furthermore, co-surfactants increase interfacial fluidity by penetrating into the surfactant film creating void space among surfactant molecules. Constraints on the formulas were placed so that the oil phase was not less than 37.5% to ensure melting of the crystallized product based on the early predictions give in Table 2, and did not exceed 63% to ensure efficient $CoQ_{10}$ emulsification.

Emulsion Droplet Size Analysis and Turbidity Measurements

Formulation (50 mg) melted at 37° C. was diluted with water, pre-equilibrated at 37° C., to 100 ml in an Erlenmeyer flask and gently mixed with hand. The resultant emulsions were evaluated for its droplet size and turbidity as follow.

The droplet size distribution of the resultant emulsions was determined by laser diffraction analysis using Coulter particle size analyzer (Model LS230, Miami, Fla.), which has a particle size measurement range of 0.04-2000•m. The sizing of the emulsions was determined in a small volume module. Samples were directly placed onto the module and the data was collected for 60 seconds. Particle size was calculated from the volume size distribution. All studies were repeated, with good agreement being found between measurements.

Turbidity of the resultant emulsions given in nephlometric turbidity units (NTU) was measured using HACH turbidimeter (Model 2100 AN, Loveland, Colo.). Turbidity measurements were performed on 30 ml of the emulsion stored in a clear screw-capped sample vials. The HACH 2100AN turbidimeter used was carefully calibrated with formalin standards. Accuracy at the lower range of turbidity is essential especially for small and diluted emulsions with high surfactant concentrations. The largest source of error at low turbidities is the stray light, that is, the light that reaches the detector due to sources other than sample turbidity. Accuracy of the HACH 2100AN turbidimeter, as specified by the manufacturer and based on instrument calibration, is approximately ±0.01 NTU with stray light less than or equal to 0.01 NTU.

Figure 6:
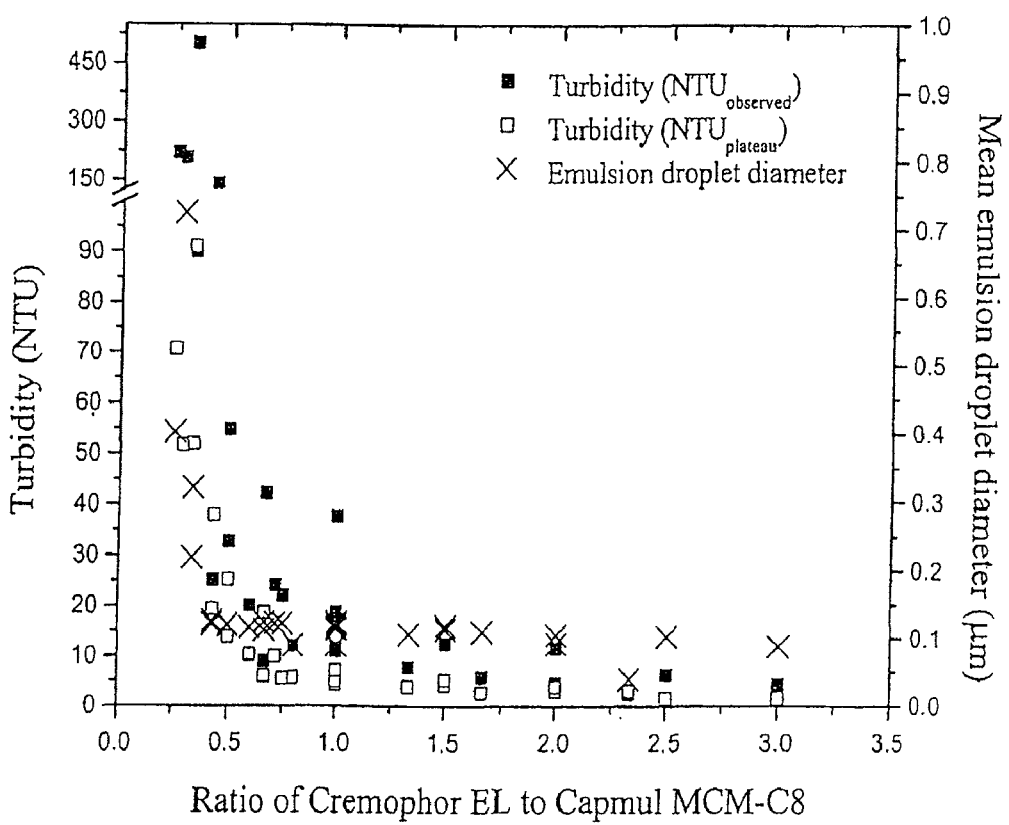
FIG. 6 is a graph showing the effect of surfactant (cremophor EL) to co-surfactant (capmul MCM-C8) ratios on mean droplet size diameter and on $NTU_{observed}$ and $NTU_{plateau}$ turbidity values.

The effect of surfactant to co-surfactant ratio on droplet size is given in FIG. 6. At ratios greater than 0.5, globule size was relatively constant at about 100 nm and independent on any component of the ternary system. It was only at ratios smaller than 0.5 when globule size increased and became greatly dependent on cremophor EL and capmul MCM-C8 concentrations yet independent on the added oil phase. It was reported that the addition of surfactant to the microemulsion systems causes the interfacial film to stabilize and condense, while the addition of co-surfactant causes the film to expand. Comparison of droplet size data with the visual observations shows that good emulsification properties are reflected by the low globule size with the exception of the formula made with high capmul MCM-C8 to cremophor EL ratios. This reflects the fact that the visual test is a measure of the spontaneity of emulsification rather than a measure of the quality of the formed emulsion.

Turbidity, given in NTU, was measured for the same samples utilized for particle size analysis. The effect of surfactant to co-surfactant ratio of the emulsified formulas on $NTU_{observed}$ and $NTU_{plateau}$ turbidity readings is given in FIG. 6. As seen in the plot, turbidity follows the same trend as droplet size. It has been reported that a linear correlation exists between the intensity of the scattered light and the squared volume of the dispersed droplets. Hence, NTU could be directly used to predict relative droplet size of the emulsion. To give a sense about the clarity of the formulas, turbidity of drinking water ranges from 0 to 1 NTU.

Fourier Transform-Infrared Spectroscopy (FT-IR)

FT-IR spectroscopy was performed using FT-IR model Nicolet Impact 410 (Thermo Nicolet, Madison, Wis.) attached to an attenuated total reflectance (ATR) accessory (DuraSampI/R, SensIR Technologies, Danbury, Conn.). ATR was fitted with a single bounce diamond at 45.degree. internally reflected incident light providing a sampling area of 1 mm in diameter with a sampling depth of several microns. Samples analyzed were $CoQ_{10}$ powder, a 50:50 $CoQ_{10}$-lemon oil melt, a solidified 50:50 $CoQ_{10}$-lemon oil mix and a solidified mixture of lemon oil, $CoQ_{10}$, cremophor EL and capful MCM-C8 at a ratio of 0.5:0.5:1:1. Samples were prepared as described above. A small amount of the sample was directly placed on the diamond disk and scanned for absorbance over the range from 4000 to 500 wavenumbers ($cm^{-1}$) at a resolution of 1 $cm^{-1}$.

Figure 7:
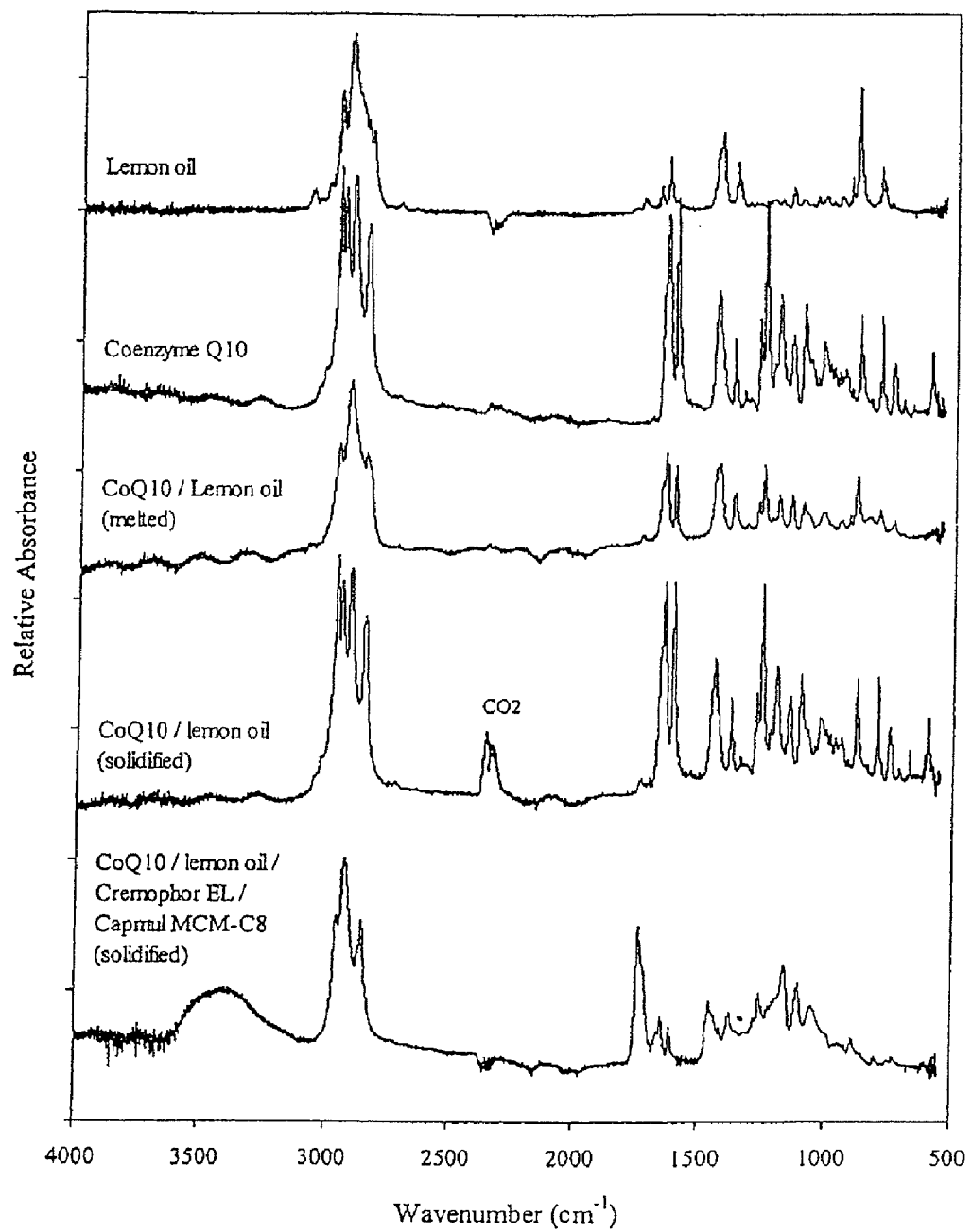
FIG. 7 shows the FT-IR spectra of $CoQ_{10}$ and lemon oil, and the effect of re-crystallization on the IR spectra of different $CoQ_{10}$ mixtures.

The ease of handling aqueous solutions and semisolid preparations is one of the major advantages of ATR used in conjugation with FT-IR spectrometry. $CoQ_{10}$ compatibility with the excipients of self-nanoemulsified preparation can be tested with FT-IR. Absorbance spectrums of $CoQ_{10}$ and lemon oil are given in FIG. 7. $CoQ_{10}$ spectrum showed several sharp characteristic peaks. The spectrum of the 50:50 melt of $CoQ_{10}$ and lemon oil, given in FIG. 7, had features of each of the components with the expected peak broadening due to its amorphous character whereas a sample of the solidified mixture had sharp lines and resembled the $CoQ_{10}$ spectrum in every detail. Lemon oil did not change the infrared spectrum of $CoQ_{10}$ indicating no chemical interaction in the binary system and that the molecular structure of $CoQ_{10}$ remained completely intact. Similarly, when cremophor EL and capmul MCM-C8 were added to the $CoQ_{10}$-lemon oil mix and the solidified mixture was analyzed, the resulting spectrum given in FIG. 7 had the characteristic $CoQ_{10}$ bands at 1608 and 1643 $cm^{-1}$ corresponding to the benzoquinone ring and the mono substituted isoprenoid units, respectively. The results obtained indicate that $CoQ_{10}$ reforms to its original crystalline state when the formulation is allowed to solidify.

Dissolution and Emulsification Studies

Dissolution profiles of the capsules filled with the self-nanoemulsified formulations were mined using USP XXIII rotating paddle apparatus (VanKel, mod. VK 7000, Cary, N.C.) at 37° C. and a rotating speed of 50 rpm in a 900 ml of water. Capsules were held to the bottom of the vessel using copper sinkers. Samples (3 ml) withdrawn after 15 min were filtered using a 10•m VanKel filter and assayed for $CoQ_{10}$ by the HPLC method reported in the HPLC analysis section. The dissolution experiments were carried out in triplicates.

Turbidity profiles of the capsules filled with the self-emulsified formulations were determined using HACH turbidimeter (Model 2100AN). Low-pressure flow cell was used to allow directly reading samples turbidity associated with capsules subjected to the same dissolution conditions as described above. Two ⅛ in. tygon tubing were connected to the pump attached to the dissolution autosampler (VanKel, mod. VK8000). First tubing was installed between the pump and the inlet of the flow cell while the other connected the pump to the dissolution vessel. Inlet of the tube connecting pump to the dissolution vessel was covered with a 40 .mu.m nylon screen and immersed into the medium so that the sample can be continuously withdrawn from a zone midway between the surface of the medium and the top of the rotating blade. Another tubing was installed to the outlet of the flow cell leading back to the dissolution vessel. Before starting, deionized water was pumped through the flow cell until a reading below 0.150 NTU was maintained. Throughout the study, dissolution medium was continuously pumped into the flow cell and back to the dissolution vessel. The turbidimeter was set so that a reading was recorded on the attached printer every 15 seconds. Turbidimetry experiments were carried out in triplicates.

Figure 8:
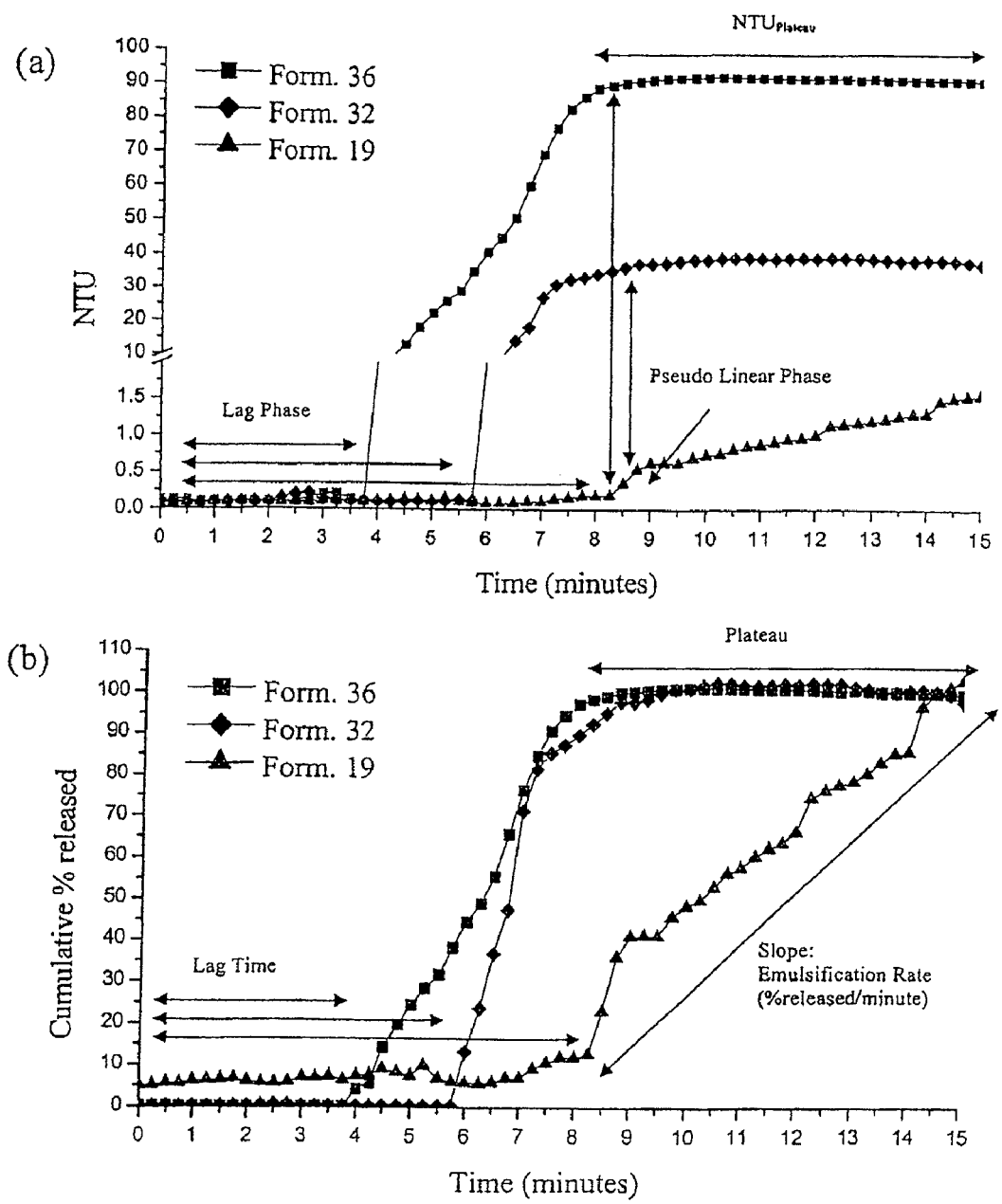
FIG. 8 shows turbidity-time profiles: a) turbidity-time profiled of three $CoQ_{10}$ SNEDDS preparation and b) normalized turbidity-time profiles showing the cumulative percent of $CoQ_{10}$ released with time for the three $CoQ_{10}$ SNEDDS preparations.

To assess spontaneity and efficacy of emulsification, turbidity of the dispersion and the relative intensity of the scattered light was correlated with time during the emulsification process. Current design confines to the standard compendia requirements for conducting dissolution experiments. Utilizing the flow through attachment, turbidity was directly measured using standard dissolution apparatus at 37° C. and controlled paddle rotating speed. Prepared formulations were filled into hydroxypropyl methylcellulose (HPMC) capsules. HPMC capsules are shown to dissolve at longer times compared with standard gelatin capsules. Average dissolution time for an HPMC capsule size 4, 3 and 0 in water at 37° C. was 300, 250 and 120 s, respectively. Extra time provided by HPMC capsules allows the formula to completely melt at body temperature before its exposure to body fluids. Representative dissolution curves monitored by turbidimetry for three formulations are shown in FIG. 8(a). Formulation 19 has 21.4% w/w $CoQ_{10}$, 21.4% w/w lemon oil, 14.3% w/w Capmul, and 42.9% w/w Cremophor. Formulation 32 has 27.3% w/w $CoQ_{10}$, 27.3% w/w lemon oil, 31.8% w/w Capmul, and 13.6% w/w Cremophor. Formulations 36 has 30.0% w/w $CoQ_{10}$, 30.0% w/w lemon oil, 30.0% w/w capmul, and 10.0% w/w cremophor. Due to large number of readings obtained, plots of turbidity against emulsification time have the characteristic lag phase, pseudo linear phase and a gradual tailing toward a plateau as the emulsion systems approached equilibrium. Actual cumulative amount of $CoQ_{10}$ released after 15 min for the preparations was measured by HPLC. $CoQ_{10}$ was completely released and dispersed from all formulations into the medium within 15 minutes.

$CoQ_{10}$ was analyzed at ambient temperature utilizing a C18, 3.9×150 mm reverse phase chromatography column (Nova-Pak; Waters, Milford, Mass.). The mobile phase consisted of methanol:n-hexane (9:1) and was pumped at a flow rate of 1.5 ml $min^{-1}$. The Waters HPLC instrument consisted of a 510 pump, 712 WISP autosampler, and a 490E UV detector set at a wavelength of 275 nm. The chromatographic data was managed using STAR 5.3 software (Varian, Walnut Creek, Calif.).

NTU values obtained for the solidified samples placed in the dissolution medium at 37° C. after reaching an equilibrium could be termed $NTU_{plateau}$. In order to demonstrate the efficacy of emulsion formation before and after solidification $NTU_{observed}$, which were previously determined for the melted samples while measuring droplet size, could be roughly correlated with $NTU_{plateau}$.

Figure 9:
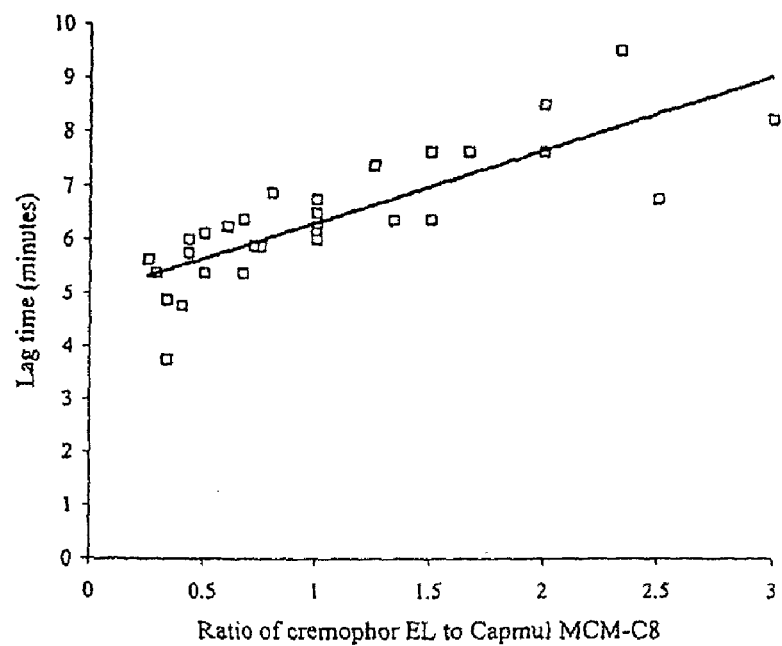
FIG. 9 is a graph showing the effect of surfactant (cremophor EL) to co-surfactant (capmul MCM-C8) ratios on lag time to self-emulsification.

Lag phase of the turbidity-time profile reflects the time elapsed before the formula is released from the capsule into the dissolution medium. FIG. 9 correlates lag times with surfactant to co-surfactant ratios. Intercept of the regression line with the y-axes was at 4.98 min which is almost identical to the average break time for an empty HPMC capsule size 4. Any deviation from this time should be correlated with the inherent properties of the fill material. Increase in cremophor EL to capmul MCM ratios from 0.5 to 3 delayed the onset of emulsion formation from 6.1 to 8.2 min, respectively. Increase in surfactant concentration delayed the onset of emulsification. At high cremophor EL concentration, progress of emulsification might be compromised by viscous liquid crystalline gel formed at the surfactant-water interface. It was reported that when a self-emulsified system is diluted by the aqueous phase various mesomorphic phases formed between the formula and the water. This was observed when the mesogenic properties of the formulation at different concentrations of each component were evaluated by studying the optical birefringence of the samples. In the absence of water, a droplet of surfactant (cremophor EL) and co-surfactant (capmul MCM-C8) placed in contact on a microscope slide revealed a boundary with no obvious signs of mixing and no optical birefringence. When cremophor EL was mixed with water in the absence of co-surfactant, the mixture showed birefringent texture of a gel. Addition of co-surfactant resulted in typical birefringent textures of non-gelled fluid lyotropic liquid crystalline phase for a system with a fixed surfactant to co-surfactant weight ratio of 1:1.

Figure 10:
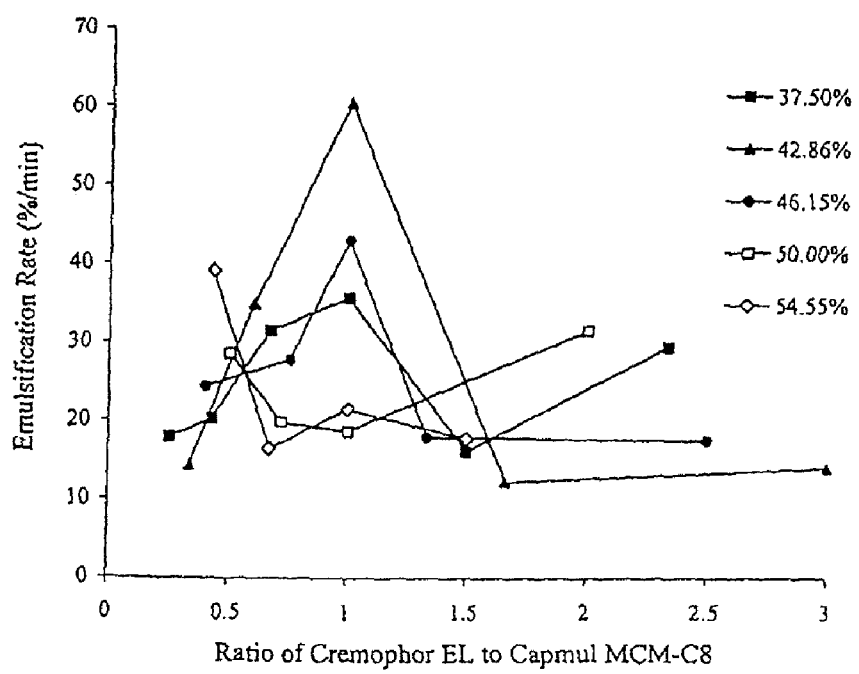
FIG. 10 is a graph showing the effect of surfactant (cremophor EL) to co-surfactant (capmul MCM-C8) ratios on the emulsification rate.

As shown in FIG. 8(b), a cumulative percent of the formulation emulsified with time could be obtain by plotting cumulative NTU.sub.plateau as a function of time, assuming that NTU.sub.plateau reflect 100% of the formula released from the capsules regardless of the actual amount of $CoQ_{10}$ dissolved in the medium. As seen from FIG. 8(b), plots of cumulative percent of the formulation released with time are identical to the original profiles correlating turbidity with time where curved characteristics mainly lag time, pseudo linear phase and plateau are preserved. This, slope of the pseudo linear phase for the line correlating cumulative percent emulsified with time could be regarded as the emulsification rate ($E_{rate}$) or emulsification efficacy. This value is very useful in comparing emulsification tendency of the self-emulsified preparation. FIG. 10 correlates emulsification rate with oil loading and surfactant to co-surfactant ratios. $E_{rate}$ is given as percent of the formula emulsified per minute. Maximum emulsification rate was obtained at a surfactant to co-surfactant ratio of 1 and oil loading of 42.6%.

EXAMPLE II

Powdered self-emulsified dosage forms provide an attractive alternative to filled-capsule preparations. The proper excipient selection, however, is crucial when formulating dry adsorbed solid formulations. The following example illustrates the various properties associated with a preferred powdered self-emulsified dosage form.

Preparation of a Solid-State Self-Nanoemulsified Dosage Form

The eutectic-based self-nanoemulsified drug delivery system (SNEDDS) of $CoQ_{10}$ was prepared as follows: $CoQ_{10}$ and lemon oil at a ratio of 1:1 were accurately weighed into screw-capped glass vials and melted in a water bath at 37° C. Cremophor EL and Capmul MCM-C8 were added to the oily mix, each at a final concentration of 26.9% w/w. The resultant emulsion was mixed with a stirring bar until a transparent solution of SNEDDS was obtained. The SNEDDS then was allowed to cool at ambient temperature for 24 hours until a viscous paste was obtained. Nanoemulsion-absorbed granular material was obtained from a mixture of SNEDDS paste, Kollidon VA 64, Glucidex IT 12, and Avicel at a ratio of 0.1 1:0.13:0.56:0.2, respectively. SNEDDS was mixed initially with Kollidon VA 64 using a mortar and pestle until a semi-solid waxy paste was obtained. The mixture then was ground with Glucidex IT 12 in the mortar for 1 min to obtain the dry microemulsion-based granules. Finally, Avicel was added to the granules and blended in a V-blender (Patterson-Kelley Co., E. Stroudsburg, Pa.) for 5 minutes. Six formulations were made, each with a different grade of Avicel MCC.

Carr's Flowability Index

The flow properties of the solid-state powdered emulsion were determined by Carr's method. Compressibility, angle of repose, angle of spatula, and uniformity coefficient were measured.

The granular powder (10 g) was poured lightly into a 25-mL graduated cylinder. The powder was tapped until no further change in volume was observed. Powder bulk density, pb ($g/cm^3$), was calculated as the weight of the powder divided by its volume before tapping. Powder tapped density, pp ($g/cm^3$), was calculated as the weight of the powder divided by its volume after tapping. The percentage of compressibility was computed from the following equation:

% compressibility=$100(P_p-P_b/P_p)$

The angle of repose was measured with a protractor for the heap of granules formed by passing 10 g of the sample through a funnel at a height of 8 cm from the horizontal surface. A steel spatula with a 5×⅞ in. blade was inserted to the bottom of the heap and withdrawn vertically. The angle of the heap formed on the spatula was measured as the angle of spatula.

The uniformity coefficient was obtained by sieve analysis of 10 g of the powdered material using a Retsch sieve shaker type AS200 (F. Kurt Retsch GmbH, Germany) fitted with eight US-standard sieves (Dual Mfg. Co., Chicago, Ill.) ranging in size from 0.075 to 1.7 mm. Uniformity coefficient is the numerical value arrived at by dividing the width of the sieve opening that will pass 60% of the sample by the width of the sieve opening that will pass 10% of the sample. The flowability index was calculated with the point scores, ranging from 0 to 100, in a scale described by Carr to evaluate the flow and the arching properties of powders.

Compaction of the Solid-State Self-Nanoemulsified Dosage Form

Microemulsion-adsorbed compacts were prepared using concave elongated punches (Natoli Engineering Co., St. Charles, Mo.). Tablets were made by compressing 1245 mg of the powder, which corresponds to 30 mg in weight of $CoQ_{10}$, between the faces of the punch. Punches were mounted between the platens of a Carver press model C (Carver Inc., Wabash, Ind.) attached to a semiautomatic compression assembly model 2826 (Carver). The compaction pressure ranged from 15.6 to 312.3 MPa. The dimensions of the compact were measured to ±0.01 mm using a dial thickness gauge (Lux Sci. Inst. Corp., New York, N.Y.). Punches were 0.750 in. long and 0.375 in. wide and provided tablets with an area of the curved segment equivalent to 0.0083 $in^3$ and a height of the curved surface above the central thickness equivalent to 0.06 in.

Determination of True Density and Compact Porosity

The true density, pt, of the powdered self-emulsified formulation was determined in triplicate using a helium pycnometer, model Ultra-pycnometer 1000 (Quantachrome, Boynton Beach, Fla.). The density of the resulting compacts, pc, was calculated from the weight and volume of the compact. The porosity, •, of the compacts was calculated by the following equation:

$$•=100(1-pc/pt)$$

Determination of Tensile Strength

Figure 11:
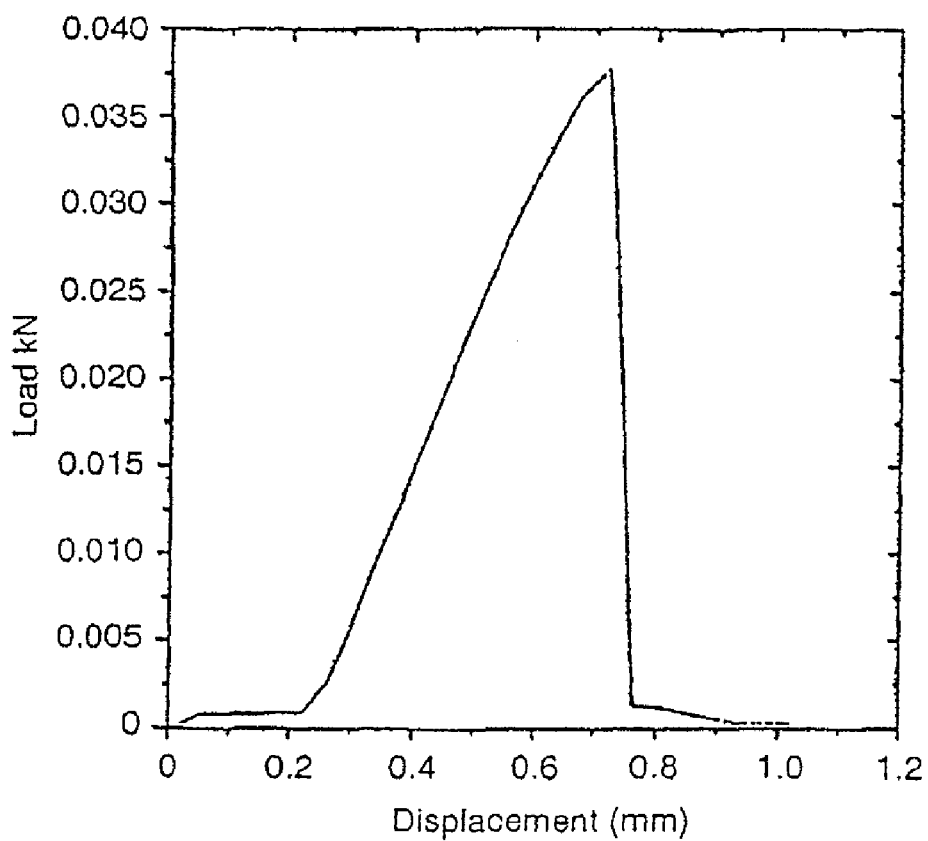
FIG. 11 is a representative load-displacement curve obtained from a three-point flexure test of self-nanoemulsified tablet dosage form.

Tensile strength provides a measure of the inherent strength of the compacted material independent of tablet dimensions. Tensile strength of the elongated, curve-faced tablets was measured in triplicate with a three-point flexure test using the Instron material-testing instrument model 4442 (Instron Corp., Canton, Mass.). The load was applied at a rate of 25 mm/min, and the fracture load was obtained from the load-displacement curve recorded using Instron software series IX. A typical load-displacement curve of the microemulsion-based tablets is shown in FIG. 11. Tablets were examined for the mode of failure, and only those with the fracture plane running through the center point of the surface of the tablet were used to derive tensile-strength values.

The tensile strength was calculated by the following equation:

$$•_f = 3FL/2d^2(d+2a/6A+bd)$$

in which $•_f$ is the tensile strength; F is the fracture load in a three-point flexure text; b and d are the width and the thickness of the tablet, respectively; a is the height of the curved surface above the central thickness; A is the area of the curved segment; and L is the distance between the lower supports.

Heckel Analysis

The densification of the dry powdered emulsion was analyzed by the out-of-die Heckel equation $$-Ln• = KP+D$$

in which P is the compaction pressure, • is the porosity of the compact, K is the slope of the linear portion of the Heckel plot, and D is a function of the original compact volume. K is equal to the reciprocal of the mean yield pressure $P_y$, which is three times the yield strength of the material. D is a constant related to the geometry of the system and the degree of packing of the particles in the die.

Measurement of Surface Roughness

The roughness profiles for the upper and lower surfaces of the compacts were measured with a Mahr perthometer concept 6.3 surface texture-measuring instrument (Mahr Federal Inc., Cincinnati, Ohio). Tablets were mounted on the X/Y table and scanned with a contact PZK drive unit using the stylus method to move the tracing arm (model MFW-250) across the surface. A tracing length of 3.5 mm was used to obtain 51 profiles with a spacing of 112•m. P-profile, waviness, and roughness parameters were computed for every profile, and the mean of all 51 profiles was collected. The following parameters were measured:

$P_s$ (profile parameter): the mean distance between local peaks of the P-profile $W_s$ (waviness parameter): the mean distance between local peaks of the W-profile $R_a$ (roughness average): the arithmetic average of the roughness profile ordinates $R_z$ (mean roughness depth of the R-profile): the arithmetic average of roughness depths (i.e., the vertical distance between the highest peak and the deepest valley of consecutive sampling lengths).

Figure 12:
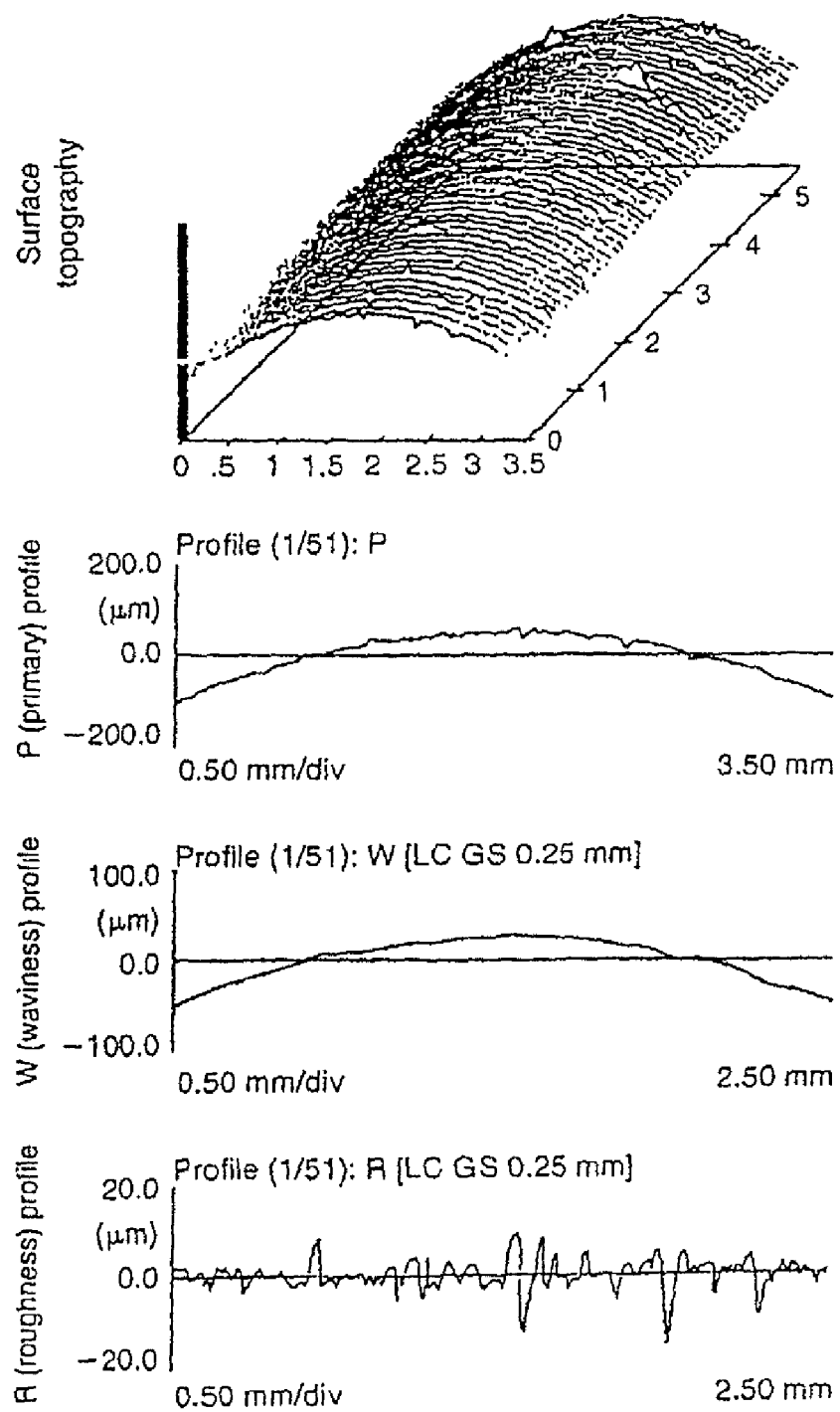
FIG. 12 is a representative surface topography, P, W, and R profiles of self-nanoemulsified tablets, obtained by a Mahr perthometer concept surface-measuring instrument.

P-profile (primary profile): the mean line generated from the traced profile. Using profile filters, P-profiles separate into long-wave (W-profile) and short-wave (R-profile) components. A representative surface topography, P, W, and R profiles, obtained by the profilometer are shown in FIG. 12.

Friability and Disintegration Studies

The friability of the compacts was measured using a VanKel type, dual-chamber drum, friability tester (VanKel, Cary, N.C.) set at a rotation speed of 25 rpm. Five grams of tablets were rotated for 4 min (100 rotations). At the end of the run the tablets were weighed accurately, and the percent friability was computed from the weight of tablets before and after the test. The disintegration time for three replicates was measured using the VanKel single-basket disintegration-testing system at 37° C. according to the USP XXIV specification.

Dissolution Studies

The dissolution profiles of the self-emulsified tablets were determined using a USP XXIV rotating basket apparatus (model VK7000, VanKel) at 37° C. The rotating speed was 50 rpm, and the dissolution medium was 900 mL of water. Samples (3 mL) withdrawn at fixed time intervals were filtered using a 10-•m VanKel filter and were assayed for $CoQ_{10}$ by HPLC at 275 nm. Briefly, $CoQ_{10}$ was analyzed using a C18 3.9×150 mm reverse-phase chromatography column (Nova-Park; Waters, Milford, Mass.). The mobile phase consisted of methanol-n-hexane (9:1) and was pumped at a flow rate of 1.5 mL/min$^{-1}$. The dissolution experiments were conducted in triplicate.

Evaluation of Flow Properties

One of the limitations of self-emulsified tablet dosage forms is the poor flow of the powdered mass that holds the oily formulation. The flowability index shown in Table 3 for the microemulsion-absorbed powdered material was obtained by measuring the powders' mechanical properties (i.e., compressibility, angle of repose, angle of spatula, and uniformity coefficient as previously discussed).

TABLE 3

| Avicel MCC Grade | Disintegration Time (min) | Tensile Strength $•_0$ (MPa) | $R^2$ | Yield Strength (MPa) | $R^2$ | Flowability Index |
|---|---|---|---|---|---|---|
| Avicel PH-105 | 47.82 (0.66) | 0.26098 | 0.987 | 14.3062 | 0.994 | 56.5 |
| Avicel PH-101 | 30.65 (0.65) | 0.35876 | 0.989 | 14.368 | 0.992 | 63.5 |
| Avicel PH-113 | 27.88 (1.5) | 0.32991 | 0.997 | 25.0627 | 0.948 | 59 |
| Avicel PH-102 | 22.775 (1.275) | 0.32834 | 0.991 | 14.43 | 0.991 | 55 |
| Avicel PH-112 | 23.475 (1.975) | 0.38837 | 0.992 | 30.8642 | 0.97 | 63 |
| Avicel PH-200 | 15.94 (1.54) | 0.34455 | 0.992 | 20.202 | 0.951 | 52 |

According to the method proposed by Carr, the flowability performance of a powder with a flow index between 60 and 69 can be described as acceptable. A higher value would indicate a still-better flow, but considering high oil loading in the formulation, the flow values obtained are reasonably good. For direct compression, these values can be improved readily by adding a low concentration of silicates such as silicon dioxide, commonly used as a glidant and anti-adherent. Good flow is the result of the granular nature of the formulations, which is enhanced primarily by the absorbing properties of Kollidon VA 64. The effect of MCC particle size on the flow properties of the preparations appeared insignificant.

Heckel Analysis of the Powdered Self-Emulsified Formulation

The Heckel equation is used often to distinguish between the mechanisms of consolidation such as plastic deformation and brittle fracture. Three types of Heckel plots were reported that distinguish between the compaction behavior of powdered material on the basis of their particle size or mixture components. Data required for Heckel analysis are obtained by either out-of-die or in-die methods. The in-die or at-pressure method collects data during the compaction of the powder. On the other hand, the out-of-die or zero-pressure method requires collecting data after the ejection of the compacts, a procedure that eliminates the effect of elastic deformation on the densification of the powder.

Figure 13:
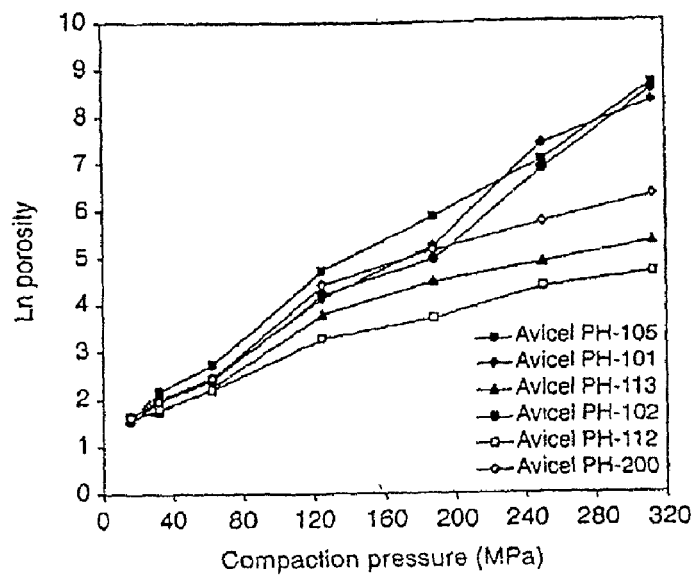
FIG. 13 is an out-of-die Heckel plot of six formulations showing the influence of the added Avicel MCC.

The out-of-die Heckel analysis of the compaction of the microemulsion-absorbed granules containing various grades of MCC is shown in FIG. 13. The Heckel plots appear to be linear over the compaction range between 15.6 and 312.3 MPa. Linear regression was performed on the data points of all the powdered materials to calculate the yield strength as previously discussed. Yield strength (see Table 3) increased by increasing the particle size of MCC grades having a 5% moisture content. This may be attributed to the effects of the initial particle size on volume reduction. In addition, absorbing oil into the surface of the powder may alter its compaction properties.

Several other researchers reported that coating the particles of various pharmaceutical powders with layers of surfactant noticeably alters their mechanical behavior when they are compressed into tablets. The degree of coating depends on the available surface area and the absorbing capacity of the powder. Formulations made with Avicel PH-105 had the lowest yield strength at 14.3 MPa (see Table 3). This probably is a result of the smaller particle size of Avicel PH-105, which provides a larger surface area for adsorption. This in turn facilitates homogeneous oil distribution throughout the compact, allows efficient particle lubrication and packing, and mediates plastic deformation. Formulations made with Avicel PH-112 and 113 had the highest yield-strength value among the compacts. Avicel PH-112 and 113 have a moisture content of no more than 1.5% and 2% respectively. The reason for the higher yield-strength value is still unclear. It might be the result of moisture-mediated surface absorption, which limits the formulations' absorbing capacity. In one reported study, moisture was found to act as a plasticizer and to influence the mechanical properties of MCC. Such a phenomenon might help retain surface characteristics and preserve tableting and compaction properties of adjuvants. The adjuvants, Avicel PH-112 and 113, were added merely to boost the compressibility of the soft oil-absorbed compacts rather than promote oil absorption.

Tableting Performance of the Powdered Self-Emulsified Formulations

To describe the tableting performance of the powdered microemulsion, compressibility, compatibility, and tabletability of the formulations were evaluated.

Figure 14:
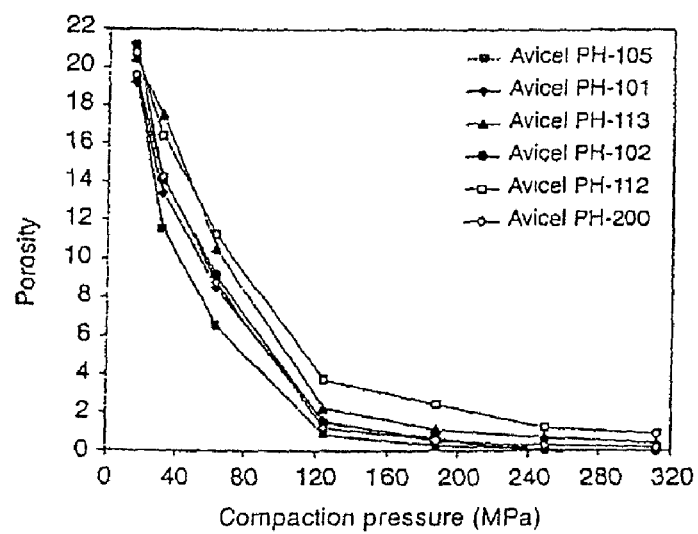
FIG. 14 is a plot of tablet porosity against compaction pressure showing the compressibility of six self-nanoemulsified powdered formulations with various grades of Avicel MCC.

Compressibility is the ability of a powdered material to undergo a reduction in porosity as a result of applied pressure. This could be represented by a plot of porosity against the applied compaction pressure, as shown in FIG. 14. Compressibility of the powders is an important factor that governs the strength of compacts, especially at lower compaction pressures. This effect is the result of the formation of a larger interparticulate bonding area and a reduction in porosity that arises from plastic deformation. Hence, the more compressible the powder, the stronger the resultant compacts. When the dry powdered microemulsion-based formulations were compressed under the same compression conditions, compacts made with Avicel PH-105 had the lowest porosity and thus were the most compressible among the adsorbed powders. This result might be attributed to the greater plasticity of the formulation containing Avicel PH-105 as indicated by its low yield strength of 14.3 MPa (see Table 3). The outcome also may be the result of the smaller particle size (20•m) of Avicel PH-105. Smaller particle size provides larger surface areas for oil adsorption and allows the powder to pack more efficiently. Avicel PH-112 and 113 showed the greatest resistance to plastic deformation at a lower compaction pressure, as observed by their higher yield strengths of 30.9 and 25.1 MPa, respectively (see Table 3). Nevertheless, all the formalities showed great dependence on compression pressure regardless of MCC particle size. The porosity of all powdered materials decreased rapidly with an increase in compaction pressure•120 MPa and reached relatively constant values thereafter.

Figure 15:
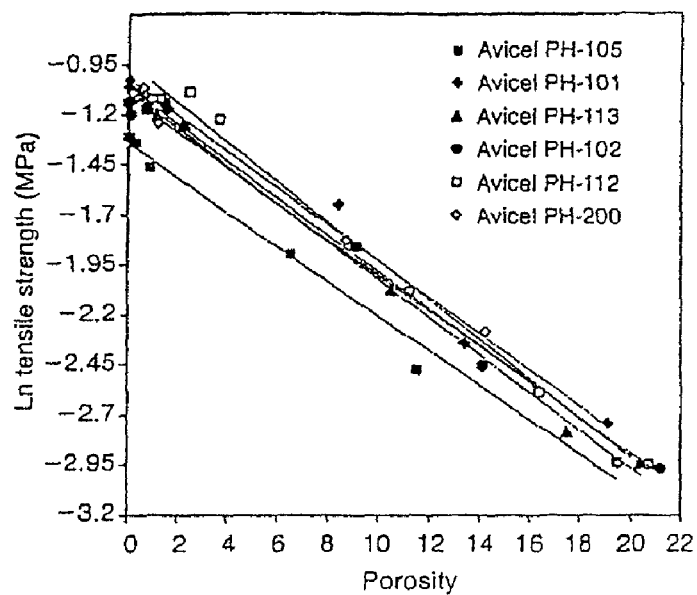
FIG. 15 is a plot of the natural logarithm of tensile strength against porosity showing the compactibility of six self-nanoemulsified powdered formulations with various grades of Avicel MCC.

Compactibility is the ability of a powdered material to produce compacts with sufficient strength under the effect densification. This can be represented by a plot of tablet tensile strength against the resultant porosity, at which tensile strength decreases exponentially with an increase in porosity, as shown in FIG. 15. This relationship can be expressed by the following equation:

$$Ln\bullet = Ln\bullet_0 - b\bullet$$

in which • is the tensile strength, •$_0$ is the tensile strength at zero porosity, b is a constant related to the pore distribution in the tablets, and • is the porosity. Tensile strength at zero porosity, •$_0$, was obtained by fitting the equation to the data followed by extrapolation. All powdered formulations followed the exponential relationship described in the equation. Tensile strength at zero porosity, •$_0$, (see Table 3) appears independent of the initial MCC particle size. The lowest •$_0$ value for compacts made with Avicel PH-105 indicates the weakest bonding, which can be attributed to its highest adsorbing capacity. This causes Avicel PH-105 particles to be fully coated with a film of the oily formulation, thereby reducing the ability for interparticulate interactions and surface bonding.

Figure 16:
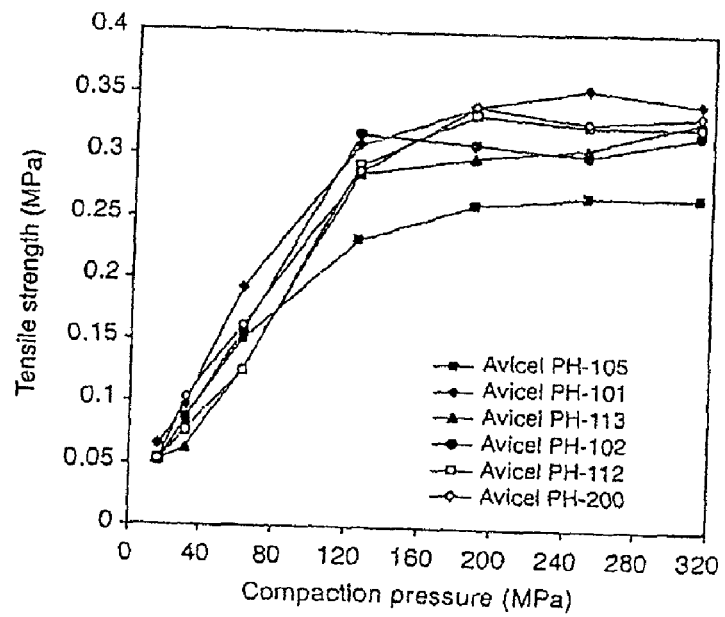
FIG. 16 is a plot of tensile strength against compaction pressure showing the tabletability of six self-nanoemulsified powdered formulation with various grades of Avicel MCC.

Tabletability is the ability of a powdered material to produce compacts with sufficient strength under the effect of compaction pressure and is represented by a plot of tablet tensile strength against compression pressure. A linear relationship between tensile strength and compaction pressure was observed for each of the formulations within the compaction range <120 MPa and reached a plateau thereafter, see FIG. 16. The effect of particle size of MCC on tensile strength appears less significant throughout the compaction range. MCC characteristics such as particle size and size distribution were found to have little effect on the tensile strength of tablets made from spray-dried Avicel. This could result form the low MCC loading of 20% in the formulation. The adsorbing capacity of MCC appeared insignificant in terms of producing compacts with distinctive tensile strengths at lower compaction pressures. At compression loads >120 MPa, during which most of the pores are eliminated, the difference in the interparticulate bonding area would be small. At a higher compression pressure, the bonding strength per unit bonding area would be the decisive factor in controlling compact strength. Consequently, Avicel PH-101, 112, and 200 showed the greater tensile strengths of 0.36, 0.39, and 0.34, respectively, at compaction pressures >120 MPa.

Surface Roughness Study

The profile parameters measured for the compacts are listed in Table 4.

TABLE 4

| Avicel MCC Grade | P-Profile | | W-profile | | R-Profile | | | |
|---|---|---|---|---|---|---|---|---|
| | $P_s$ (•m) | | $W_s$ (•m) | | $R_a$ (•m) | | $R_z$ (•m) | |
| | Upper | Lower | Upper | Lower | Upper | Lower | Upper | Lower |
| Avicel PH-105 | 118.2 | 151.68 | 391.02 | 446.9 | 2.97 | 1.83 | 20.07 | 12.84 |
| Avicel PH-101 | 123.82 | 157.09 | 373.9 | 486.62 | 1.84 | 1.63 | 12.92 | 11.6 |
| Avicel PH-113 | 143.6 | 144.24 | 384.26 | 427.14 | 1.96 | 1.84 | 14.26 | 13.08 |
| Avicel PH-102 | 156.78 | 173.51 | 386.88 | 469.76 | 1.48 | 1.31 | 10.62 | 9.26 |
| Avicel PH-112 | 152.31 | 160.58 | 357.12 | 405.87 | 1.85 | 1.59 | 13.53 | 10.91 |
| Avicel PH-200 | 162.34 | 175.16 | 387.62 | 431.95 | 1.77 | 1.52 | 12.57 | 11.04 |

Waviness of the lower surface of the tablets, exposed to the lower punch during compaction, was greater than that of the upper surface of the compacts. This is apparent from the W and P profiles given as $W_s$ and $P_s$ parameters, respectively. Higher values of the $W_s$ parameter for the lower surface of the tablets might be the result of the segregation of the larger granules to the bottom of the die during powder filling. These granules are the Kollidon VA 64-based paste ground with maltodextrin. Segregation was visually evident by the higher degree of mottling of the lower surface caused by the colored granules when compared with the extragranular white MCC powder. However, no change in surface waviness was observed as a function of the initial MCC particle size.

On the other hand, the P-profile measures both roughness and waviness of the surface. Both granule segregation and MCC particle size induced the $P_s$ parameter, which is a measure of the distance between grooves primarily caused by granules of variable sizes. Higher $P_s$ values of the lower surface of the compacts indicate that surface waviness is the dominant factor in determining the $P_s$ parameter. $P_s$ increased with an increase in particle size from Avicel PH-105 to Avicel PH-200. This is probably because larger-size MCC provides greater spacing between the particles. Because of the powder segregation, the lower punch is exposed to a larger portion of the granules that contain the lipid-based formulation. This in turn provides lubrication to the surface of the punch during tablet compaction and ejection. As a consequence, the roughness profile of the lower surface of the compacts given as $R_a$ and $R_z$ was lower than that of the upper surface of the tablets exposed to the less-lubricated upper punch. However, the MCC particle size was less significant in terms of the roughness parameters. This outcome is attributable to the fact that $R_a$ and $R_z$ are measures of the heights and depths of the peaks and valleys formed on the surface of the tablets as a result of powder compaction. Plastic deformation might have diminished the differences between MCC particles when they were monitored vertically yet maintained their characteristic boundaries detected by the P-profile parameters.

Friability Study

Figure 17:
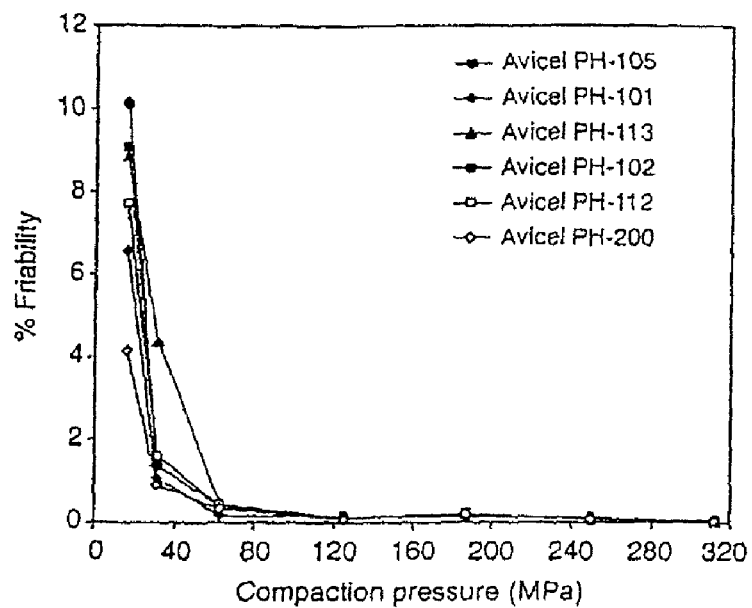
FIG. 17 is a plot of the percent friability against compaction pressure of six self-nanoemulsified powdered formulations with various grades of Avicel MCC.
Figure 18:
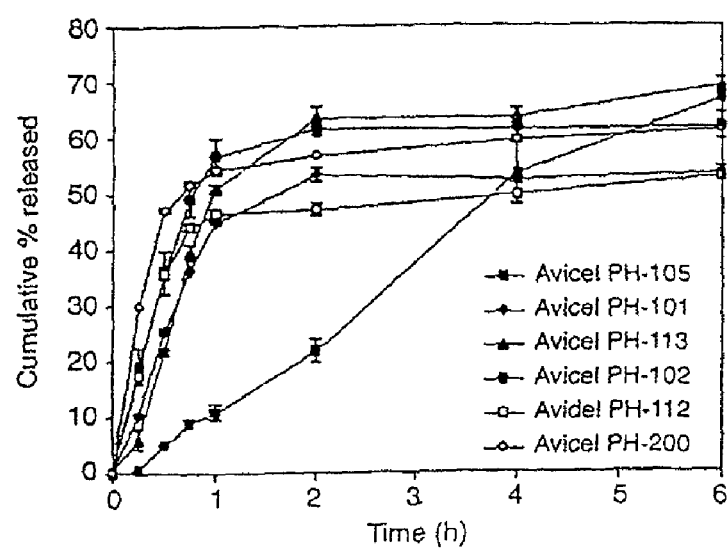
FIG. 18 is a dissolution plot showing the cumulative percent of $CoQ_{10}$ release with time from six self-nanoemulsified tablet formulations with various grades of Avicel MCC.

Friability of the compacts made from the powdered self-emulsified system as a function of compaction pressure is shown in FIG. 17. Friability decreased gradually with an increase in compression load and reached a plateau of <0.1% at compression pressures >120 MPa independent of the initial MCC particle size. No effect of MCC grade and size was evident in terms of the friability of the compacts. This correlates well with the compressibility and tabletability data. Porosities and tensile strengths for all the preparations reached their optimum values at 120 Mpa, reflecting the greatest interparticulate bonding that was further induced by oil bridging the particles Dissolution Study To evaluate the emulsion release from the absorbing compacts, dissolution studies were performed for tablets prepared at a low compaction pressure of 31.2 MPa. Ideally, SNEDDS should be released from the tablets and completely emulsify into the dissolution medium. This effect was evaluated by measuring the cumulative percent of the drug solubilized into the aqueous medium as part of the released emulsion. Dissolution plots of the self-emulsified tablets are shown in FIG. 18. The dissolution rate within the first 45 min appeared to be dependent on MCC particle size. The cumulative percent of $CoQ_{10}$ solubilized in 45 min for compacts made with Avicel PH-200, 102, 112, 113, 101 and 105 was 51.5, 49, 44, 39.5, 36, and 8.7%, respectively. After 1 hour, dissolution reached a plateau with an average release of 55% (except for Avicel PH-105). Poor $CoQ_{10}$ dissolution might be the result of an irreversible hydrophobic interaction between $CoQ_{10}$ and MCC. Initial powder compaction and slow disintegration (see Table 3) also might have induced irreversible surface adsorption to the soluble excipients of the formulation. This process causes variable release rates. Oily components of the formulation are emulsified into the aqueous medium at a faster rate compared with the release of $CoQ_{10}$. However, tablets made with Avicel PH-105 induced sustained release of $CoQ_{10}$ in a time span of 6 hours. As previously discussed, tablets made with Avicel PH-105 had the least yield and tensile strength and the lengthiest disintegration time (see Table 3). This suggests oil-induced bridging and sticking between the Avicel particles, an outcome that provides a greater area of contact. The increase in the cohesion between the particles accounts for delayed release rates without increasing the hardness of the tablets.

Although the present invention has been disclosed in terms of a preferred embodiment, it will be understood that numerous additional modifications and variations could be made thereto without departing from the scope of the invention as defined by the following claims.

The invention claimed is:

1. A method of preparing an orally administered dietary supplement comprising the steps of:
   (a) admixing coenzyme Q10 and a sufficient amount of a volatile essential oil to reduce the melting point of coenzyme Q10 to 37° C. or below; and
   (b) introducing the mixture from (a) into a hard or soft gelatin capsule, wherein the mixture forms a solution or oily melt at 37° C. or below.

2. The method of claim 1, wherein step (a) further comprises the step of adding a surfactant or a co-surfactant or both.

3. The method of claim 2, wherein the surfactant is a high HLB, and the co-surfactant is a low HLB surfactant.

4. The method of claim 2, wherein the ratio of surfactant to co-surfactant is at least about 0.5.

5. The method of claim 1, wherein the volatile essential oil is spearmint oil.

6. The method of claim 1, wherein the volatile essential oil is peppermint oil.

7. The method of claim 1, wherein the volatile essential oil is lemon oil.

8. The method of claim 1, wherein the volatile essential oil is anise oil.

9. A method of forming a compressible self-nanoemulsified drug powder comprising the steps of:
  (a) admixing coenzyme Q10 and a sufficient amount of a volatile essential oil to reduce the melting point of coenzyme Q10 to 37° C. or below, and thereby forming a solution or oily melt at 37° C. or below;
  (b) admixing at least one surfactant to the mixture from (a);
  (c) cooling the mixture from (b) to form a paste;
  (d) admixing the paste and a pyrrolidone copolymer;
  (e) admixing maltodextrin and the mixture from (d) to form granules; and
  (f) admixing microcrystalline cellulose (MCC) and the granules from (e), wherein the resulting self-nanoemulsified drug powder is capable of being compressed into a tablet.

10. The method of claim 9, wherein step (b) further comprises the step of adding a co-surfactant.

11. The method of claim 10, wherein the ratio of surfactant to co-surfactant is at least about 0.5.

12. The method of claim 11, wherein the surfactant is a high HLB, and the co-surfactant is a low HLB surfactant.

13. The method of claim 9, wherein the copolymer is a vinylpyrrolidone and vinyl acetate copolymer.

14. The method of claim 9, wherein the amount of copolymer added is from about 3% to about 35% by weight relative to the weight of the paste.

15. The method of claim 9, wherein the amount of MCC added is from about 11% to about 47% by weight relative to the weight of the paste.

16. The method of claim 9, wherein the amount of maltodextrin added is from about 35% to about 82% by weight relative to the weight of the paste.

17. The method of claim 9, wherein the amount of coenzyme Q10 is sufficient to effectuate a pharmacological effect.

18. The method of claim 9, wherein the amount of coenzyme Q10 is 70% or less by weight.

19. The method of claim 9, further including the step of compressing the resulting self-nanoemulsified drug powder into a tablet.

* * * * *

UNITED STATES PATENT AND TRADEMARK OFFICE
CERTIFICATE OF CORRECTION

| | | |
|---|---|---|
| PATENT NO. | : 8,158,162 B2 | Page 1 of 1 |
| APPLICATION NO. | : 12/493406 | |
| DATED | : April 17, 2012 | |
| INVENTOR(S) | : Mansoor A. Khan and Sami Nazzal | |

It is certified that error appears in the above-identified patent and that said Letters Patent is hereby corrected as shown below:

Cross-Reference to Related Applications:

Column 1, lines 7-8, "U.S. Pat. No. 7,588,789" should read --U.S. Pat. No. 7,588,786--

Signed and Sealed this
Ninth Day of October, 2012

David J. Kappos
*Director of the United States Patent and Trademark Office*